United States Patent [19]
Kaleta et al.

[11] Patent Number: 6,153,176
[45] Date of Patent: Nov. 28, 2000

[54] LOW PH SUNSCREEN COMPOSITIONS

[75] Inventors: James Edward Kaleta, Landen; Carlos Gabriel Linares, Loveland; Steve Gary Fishter, Harrison, all of Ohio

[73] Assignee: The Procter & Gamble Company, Cincinnati, Ohio

[21] Appl. No.: 08/818,092

[22] Filed: Mar. 14, 1997

Related U.S. Application Data

[63] Continuation of application No. 08/375,870, Jan. 20, 1995, abandoned.

[51] Int. Cl.⁷ ....................................................... A61K 7/44
[52] U.S. Cl. ............................................. 424/60; 424/401
[58] Field of Search ................................ 424/59, 401, 60

[56] References Cited

U.S. PATENT DOCUMENTS

| | | | |
|---|---|---|---|
| 4,671,956 | 6/1987 | Bouillon et al. | 424/59 |
| 4,707,354 | 11/1987 | Garlen et al. | 424/47 |
| 4,988,501 | 1/1991 | Goscinak | 424/59 |
| 5,207,998 | 5/1993 | Robinson et al. | 424/59 |
| 5,208,011 | 5/1993 | Vaughan | 424/59 |
| 5,256,404 | 10/1993 | Martino et al. | 424/59 |

FOREIGN PATENT DOCUMENTS

| | | | |
|---|---|---|---|
| 92/18832 | 1/1993 | Australia | A61K 31/415 |
| 275719 | 7/1988 | European Pat. Off. | A61K 7/42 |
| 531192 | 3/1993 | European Pat. Off. | A61K 7/00 |
| 557089 | 8/1993 | European Pat. Off. | A61K 7/42 |
| 581955 | 2/1994 | European Pat. Off. | A61K 7/42 |
| 3112943 | 10/1982 | Germany | A61K 7/42 |
| 4203072 | 11/1992 | Germany | A61K 31/415 |
| 02279621 | 11/1990 | Japan | A61K 7/42 |

OTHER PUBLICATIONS

Givaudan–Roure, product information brochure, PARSOL® HS, undated.

Haarmann and Reimer Corporation, product information brochure—Neo Heliopan sunscreen filters, unnumbered pages relating to Neo Heliopan, Type Hydro, 1992.

E. Merck, product information brochure, Eusolex®, UV filters for cosmetics, Aug. 2, 1990, pp. 49–54.

Schrader et al., CAS Abstract No. 112; 11779, of The Inhibition of Light Damage to Skin, Perfuem Kosmet, 70(8), 460–462 (1989).

*Primary Examiner*—Thurman K. Page
*Attorney, Agent, or Firm*—George W. Allen; Fumiko Tsuneki

[57] ABSTRACT

The present invention relates to low pH topical sunscreen compositions which utilize unneutralized, 2-phenylbenzimidazole-5-sulfonic acid as the sunscreen active. These compositions exhibit good sunscreening efficacy and are highly substantive to the skin.

18 Claims, No Drawings

LOW PH SUNSCREEN COMPOSITIONS

This is a continuation of application Ser. No. 08/375,870, filed Jan. 20, 1995 now abandoned.

TECHNICAL FIELD

The present invention relates to low pH topical sunscreen compositions which utilize 2-phenylbenzimidazole-5-sulfonic acid in its unneutralized, free-acid form as the sunscreen active.

BACKGROUND OF THE INVENTION

The damaging effects of sunlight on skin are well documented. Contrary to what most people believe, it is not necessary that one sunbathe to suffer the ill-effects of excessive ultraviolet (UV) exposure. In fact, significant damage can be caused by routine day-to-day activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e. sunburn). The 290 to 320 nanometer wavelength ultraviolet radiation range, designated as the "UVB" wavelength range, tends to be the primary cause of erythema, although the 320 to 400 nanometer wavelength ultraviolet radiation range, designated as the "UVA" wavelength range, also produces erythema.

In addition to the short term hazard of erythema, there are also long term hazards associated with UV radiation exposure. One of these long term hazards is malignant changes in the skin surface. Numerous epidemiologic studies demonstrate a strong relationship between sunlight exposure and human skin cancer.

Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983; which are incorporated herein by reference in their entirety. Hence, although the immediate effects of ultraviolet radiation may be cosmetically and socially gratifying, the long-term hazards are cumulative and potentially serious. Therefore, photoprotection against ultraviolet radiation is necessary.

The fact that these effects are taken seriously by the general public is suggested by considering the sun protection product market. This market has grown considerably in recent years and many new products are introduced each year. What used to be looked upon as a seasonal business is no longer such. Sun protection compounds are now included in a diversity of personal care products, particularly cosmetic-type products which are worn on a daily basis.

The most common agents for sun protection are sunscreens. These agents exert their effects through chemical means, i.e., they absorb ultraviolet radiation so that it cannot penetrate the skin. Sunscreens present the user with several problems. For example, they must be on the surface of the skin at the time of exposure to be effective. Sunscreens are preventative so one must anticipate being in the sun. To be most effective, sunscreens must be on the skin as a continuous uniform film. Delivering such a film to the uneven surface of the skin is very difficult. Also, chemical sunscreens tend to migrate on or penetrate through the skin, thereby reducing their protective effect and potentially causing adverse reactions such as burning and stinging of the skin and eyes, and other more serious allergic and toxic reactions. Therefore, a need exists to develop sun protection products which maintain their efficacy and which can be used on the sensitive facial area without causing adverse reactions.

The sunscreening agent 2-phenylbenzimidazole-5-sulfonic acid is a known sunscreening agent, and is listed as a Category I material in "Sunscreen Drug Products for Over-the-Counter Human Use; Tentative Final Monograph; Proposed Rule", Federal Register vol. 58, no. 90, 28194, May 12, 1993, which is incorporated by reference herein in its entirety. However, 2-phenylbenzimidazole-5-sulfonic acid is utilized as a neutralized, water-soluble salt, rather than as the free acid. See E. Merck Technical Pamphlet No. 03-304111, entitled "Eusolex® UV Filters For Cosmetics", Feb. 8, 1990, and Haarman & Reimer Technical Pamphlet No. R221e, entitled "Neo Heliopan Sunscreen Filters," Feb. 1993, which are both incorporated by reference herein in their entirety. Using this sunscreen as a neutralized, water-soluble salt has the disadvantage of yielding a nonsubstantive sunscreening composition which is easily removed by water and perspiration, thereby resulting in greatly diminished sunscreen protection.

Conversely, the free acid form of 2-phenylbenzimidazole-5-sulfonic is generally not utilized because of its low water-solubility and perceived formulation limitations and reduced sunscreening efficacy. In other words, it is generally believed that 2-phenylbenzimidazole-5-sulfonic acid is not suitable for formulation into a low pH composition because it would exist predominantly in the free acid form and would crystallize out of the formulation. However, there are many instances when a low pH sunscreen formulation is desired, as when formulating an acidic active such as salicylic acid or lactic acid into the product. Therefore, the need exists for developing low pH compositions which also provide adequate sun protection.

It has been found in the present invention that 2-phenylbenzimidazole-5-sulfonic acid can be formulated into aqueous compositions which have an acidic, i.e. low pH. It has been found that the neutral free acid form of the 2-phenylbenzimidazole-5-sulfonic acid, despite its low-water solubility, provides compositions having good sunscreening efficacy. These compositions also have the further advantage of not burning or stinging the skin and of having reduced eye irritation potential. Without being limited by theory, it is believed that the unneutralized free acid form of the sunscreen is less likely to penetrate through the skin or migrate into the eyes when applied upon the face. Also, the sunscreen, in its free acid form is believed to be more substantive because it is less likely to be removed by moisture. Therefore, the compositions of the present invention which utilize the unneutralized, free acid form of 2-phenylbenzimidazole-5-sulfonic acid, provide benefits such as improved substantivity, less product migration, increased UV absorption, less burning, stinging, and other undesirable skin reactions, and better compatibility with acidic formulation components. Also, another benefit of utilizing the unneutralized 2-phenylbenzimidazole-5-sulfonic acid is that high SPF efficacy is achieved without the need for using high levels of additional sunscreen materials, which can negatively affect product aesthetics or increase product cost.

It is, therefore, an object of the present invention to provide topical sunscreen compositions which provide protection of human skin from the harmful effects of ultraviolet radiation which utilize the unneutralized free acid form of the sunscreen agent 2-phenylbenzimidazole-5-sulfonic acid.

It is another object of the present invention to provide topical sunscreen compositions which have an acidic pH and which are compatible with other acidic components.

It is another object of the present invention to provide topical sunscreen compositions having enhanced substantivity, such as resistance to rub-off, water, and perspiration.

It is another object of the present invention to provide topical sunscreen compositions which are safe and nontoxic and which have less potential to burn or sting the skin or migrate into the eyes.

It is another object of the present invention to provide methods for protecting human skin from the harmful effects of ultraviolet radiation.

These and other objects will become readily apparent from the detailed description which follows.

SUMMARY OF THE INVENTION

The present invention relates to a topical sunscreen composition having a pH of less than 7 comprising:
(a) from about 0.05% to about 10% of 2-phenylbenzimidazole-5-sulfonic acid, and
(b) from about 20% to about 99.95% of a topical carrier, wherein the 2-phenylbenzimidazole-5-sulfonic acid is substantially present in free acid form in the composition.

All percentages and ratios used herein are by weight and all measurements made are at 25° C., unless otherwise designated. The invention hereof can comprise, consist of, or consist essentially of, the essential as well as optional ingredients and components described herein.

DETAILED DESCRIPTION OF THE INVENTION

The term "low pH" as used herein means a composition having an acidic pH value, i.e. a pH of less than 7. The compositions of the present invention preferably have a pH of less than about 6.5. The compositions more preferably have a pH from about 1 to about 6, even more preferably from about 1.5 to about 5, and most preferably from about 2 to about 4.

The term "topical carrier," as used herein, is well-known to one of ordinary skill in the art, and means one or more compatible solid or liquid filler diluents or vehicles which are suitable for administration to human skin. The term "compatible," as used herein, means that the components of the topical carrier are capable of being comingled with the 2-phenylbenzimidazole-5-sulfonic acid, and with each other, in such a manner that there is no interaction which would substantially reduce the efficacy or aesthetics of the sunscreen compositions under ordinary use situations. The topical carrier must be a pharmaceutically-acceptable carrier. The term "pharmaceutically-acceptable", as used herein, means that the topical carrier must be of sufficiently high purity and be suitable for use in contact with human skin without undue toxicity, incompatibility, instability, allergic response, and the like.

2-PHENYLBENZIMIDAZOLE-5-SULFONIC ACID

The present invention comprises from about 0.05% to about 10%, preferably from about 0.5% to about 10%, and more preferably from about 1% to about 4% by weight of 2-phenylbenzimidazole-5-sulfonic acid.

The sunscreening agent 2-phenylbenzimidazole-5-sulfonic acid has the Chemical Abstracts Service (CAS) Registry No. 27503-81-7, conforms to the chemical formula $C_{13}H_{10}N_2O_3S$, and can be depicted by the following chemical structure.

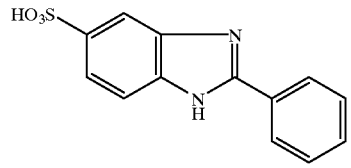

The sunscreening agent 2-phenylbenzimidazole-5-sulfonic acid is described in *CTFA International Cosmetic Ingredient Dictionary*, fifth edition, 1993, at page 539, which is incorporated by reference herein in its entirety. This sunscreen material is an acidic compound having a pKa value of approximately 4.7, and is predominantly converted into a water-soluble salt at pH values greater than the pKa value. This sunscreening agent is commercially available as Eusolex® 232 from Rona Chemical & Pigments Division, Hawthorne, N.Y., as Neo Heliopan, Type Hydro, from Haarman & Reimer Corporation, Springfield, N.J., and as Parsol® HS from Givaudan Corp., Clifton, N.J.

The sunscreening agent 2-phenylbenzimidazole-5-sulfonic acid, is well known as a sunscreening agent when it has been neutralized to form a water-soluble salt, such as, for example, the sodium, monethanolammonium, or triethanolammoium salt. See E. Merck Technical Pamphlet No. 03-304111, entitled "Eusolex® UV Filters For Cosmetics," Feb. 8, 1990, and Haarman & Reimer Technical Pamphlet No. R221e, entitled "Neo Heliopan Sunscreen Filters," Feb. 1993, which have already been incorporated by reference herein in their entirety.

In the present invention, the 2-phenylbenzimidazole-5-sulfonic acid is used such that it is substantially present in free acid form, i.e. the acid material is substantially unneutralized. The term "substantially present in free acid form," as used in reference to the 2-phenylbenzimidazole-5-sulfonic acid, means that about 90 mole percent or greater, preferably about 95 mole percent or greater, and more preferably about 99 mole percent or greater of the total amount of the 2-phenylbenzimidazole-5-sulfonic acid in the compositions of the present invention is in the free acid form. The actual percent of the free acid form of the 2-phenylbenzimidazole-5-sulfonic acid present in the compositions of the present invention will depend upon the pH of the composition.

TOPICAL CARRIER

The present invention comprises from about 20% to about 99.95%, preferably from about 50% to about 99%, and more preferably from about 75% to about 95%, by weight of a topical carrier for the 2-phenylbenzimidazole-5-sulfonic acid, and any other optional components of the present invention.

The sunscreening agent of the present invention can be formulated into a wide variety of product types, including creams, lotions, milks, mousses, gels, tonics, sprays, hand and body lotions, cold creams, facial moisturizers, anti-acne preparations, topical analgesics, make-ups, lipsticks, and the like. The topical carrier and any additional components required to formulate such products vary with product type and can be routinely chosen by one skilled in the art.

The topical carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include aqueous-based single phase solvents, e.g., water, alcohols, glycols, polyols, and the like. Examples of topical carrier systems useful in the present invention are described in the following references, all of which are incorporated herein by reference in their entirety: "Sun Products Formulary," Cosmetics & Toiletries, vol. 105, pp. 122–139 (Dec. 1990); "Sun Products Formulary," Cosmetics & Toiletries, vol. 102, pp. 117–136 (Mar. 1987); U.S. Pat. No. 4,960,764 to Figueroa et al., issued Oct. 2, 1990; U.S. Pat. No. 4,254,105 to Fukuda et al., issued Mar. 3, 1981; U.S. Pat. No. 4,976,953, to Orr et al., issued Dec. 11, 1990; and U.S. Pat. No. 5,073,372, to Turner et al., issued Dec. 17, 1991.

In the present invention, it is found that oil-in-water emulsions are highly preferred. These emulsions have light, nongreasy aesthetics, which are ideal for application to the skin, especially to facial areas. In these oil-in-water emulsions the pH can be readily maintained in the desired acidic range by utilizing a wide variety of acidic materials and buffering agents, for example benzoic acid, salicylic acid, and citric acid.

Other forms of topical carriers are also useful. When the sunscreening composition is an aerosol spray or mousse, the carrier can also utilize any of the conventional propellants to deliver the material as a foam (in the case of a mousse) or as a fine, uniform spray (in the case of an aerosol). Examples of suitable propellants include materials such as trichlorofluoromethane, dichlorodifluoromethane, difluoroethane, dimethylether, propane, n-butane or isobutane. A more complete disclosure of propellants useful herein can be found in Sagarin, Cosmetics Science and Technology, 2nd Edition, Vol. 2, pp. 443–465 (1972), which is incorporated herein by reference in its entirety.

Suitable spray containers are well known in the art and include conventional, non-aerosol pump sprays, i.e., "atomizers," aerosol containers or cans having propellant, as described above, and also pump aerosol containers utilizing compressed air as the propellant. Pump aerosol containers are disclosed, for example, in U.S. Pat. No. 4,077,441, Mar. 7, 1978, Olofsson and U.S Pat. No. 4,850,577, Jul. 25, 1989, both incorporated by reference herein, and also in U.S. Ser. No. 07/839,648, Gosselin, Lund, Sojka, and Lefebvre, filed Feb. 21, 1992, "Consumer Product Package Incorporating A Spray Device Utilizing Large Diameter Bubbles." Pump aerosols hair sprays using compressed air are also currently marketed by The Procter & Gamble Company under their tradename VIDAL SASSOON AIRSPRAY hair sprays.

Additional Components

A wide variety of additional components can be employed in the topical sunscreen compositions herein. Non-limiting examples include the following:

Pharmaceutical Actives

The compositions of the present invention can comprise a safe and effective amount of a pharmaceutical active. The phrase "safe and effective amount," as used herein, means an amount of an active high enough to significantly or positively modify the condition to be treated, but low enough to avoid serious side effects (at a reasonable benefit/risk ratio), within the scope of sound medical judgement. A safe and effective amount of the pharmaceutical active will vary with the specific active, the ability of the composition to penetrate the active through the skin, the amount of composition to be applied, the particular condition being treated, the age and physical condition of the patient being treated, the severity of the condition, the duration of the treatment, the nature of concurrent therapy, and like factors.

The pharmaceutical actives which can be used in the compositions of the present invention preferably comprise from about 0.01% to about 30% by weight of the compositions, more preferably from about 0.1% to about 10%, and most preferably from about 0.1% to about 5%. Mixtures of pharmaceutical actives may also be used.

Nonlimiting examples of pharmaceutical actives can include those which follow. It is to be understood that the active materials listed below can have more than one function and that the listing of a material in any particular class is not intended as a limitation for that material. It is also to be understood that even though the term pharmaceutical active is used, the term is non-limiting in that the actives listed herein can alternatively provide cosmetic and other types of benefits. Pharmaceutical actives useful herein include those selected from the group consisting of anti-acne actives, anti-skin wrinkling actives, non-steroidal anti-inflammatory drugs, antipruritic drugs, anesthetic drugs, antimicrobial drugs, additional sunscreening agents, sunless tanning agents, skin bleaching agents, and mixtures thereof.

Useful pharmaceutical actives in the compositions of the present invention include anti-acne drugs. Anti-acne drugs for use in the present invention include the keratolytics such as salicylic acid, sulfur, lactic acid, glycolic, pyruvic acid, resorcinol, and N-acetylcysteine; retinoids such as retinoic acid and its derivatives (e.g., cis and trans); antibiotics and antimicrobials such as benzoyl peroxide, octopirox, erythromycin, zinc, tetracyclin, triclosan, azelaic acid and its derivatives, phenoxy ethanol and phenoxy propanol, ethylacetate, clindamycin and meclocycline; sebostats such as flavinoids; alpha and beta hydroxy acids; and bile salts such as scymnol sulfate and its derivatives, deoxycholate, and cholate. Preferred anti-acne actives are those selected from the group consisting of salicylic acid, sulfur, resorcinol, lactic acid, zinc, erythromycin, benzoyl peroxide, and mixtures thereof. Preferred anti-acne agents include those selected from the group consisting of salicylic acid, benzoyl peroxide, sulfur, resorcinol, zinc, erythromycin, and mixtures thereof.

Useful pharmaceutical actives in the compositions of the present invention include non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including, but not limited to, aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Useful pharmaceutical actives in the compositions of the present invention include anti-skin wrinkling actives which help to ameliorate the effects of skin aging. Nonlimiting examples of these materials include those selected from the group consisting of salicylic acid, retinoic acid, and α-hydroxy and α-keto acids having from about 2 to about 30 carbon atoms, including compounds such as glycolic acid, lactic acid, pyruvic acid, and mixtures thereof. Preferred is salicylic acid.

Useful pharmaceutical actives in the compositions of the present invention include antipruritic drugs. Antipruritic drugs preferred for inclusion in compositions of the present invention include pharmaceutically-acceptable salts of methdilizine and trimeprazine.

Useful pharmaceutical actives in the compositions of the present invention include anesthetic drugs. Anesthetic drugs preferred for inclusion in compositions of the present invention include pharmaceutically-acceptable salts of lidocaine, bupivacaine, chlorprocaine, di-bucaine, etidocaine, mepivacaine, tetracaine, dyclonine, hexylcaine, procaine, cocaine, ketamine, pramoxine, phenol, and mixtures thereof.

Useful pharmaceutical actives in the compositions of the present invention include antimicrobial drugs (antibacterial, antifungal, antiprotozoal and antiviral drugs). Antimicrobial drugs preferred for inclusion in compositions of the present invention include pharmaceutically-acceptable salts of b-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial drugs preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate, clotrimazole, and mixtures thereof.

Also useful herein are additional sunscreening agents, i.e. sunscreening agents which can be used in addition to the 2-phenylbenzimidazole-5-sulfonic acid. A wide variety of additional sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Preferred among the additional sunscreens are those selected from the group consisting of 2-ethylhexyl p-methoxycinnamate, 2-ethylhexyl N,N-dimethyl-p-aminobenzoate, p-aminobenzoic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, triethanolamine salicylate, titanium dioxide, zinc oxide, silica, iron oxide, and mixtures thereof.

Still other useful additional sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl) methylaminobenzoic acid ester of 2,4-dihydroxybenzophenone, 4-N,N-(2-thylhexyl) methylaminobenzoic acid ester with 4-hydroxydibenzoylmethane, 4-N,N-(2-ethylhexyl) methylamino-benzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Generally, the additional sunscreens can comprise from about 0.1% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Also useful in the present invention are sunless tanning agents including dihydroxyacetone, glyceraldehyde, indoles and their derivatives, and the like, with dihydroxyacetone being preferred.

Other useful actives include skin bleaching (or lightening) agents including, but not limited to, hydroquinone, ascorbic acid, kojic acid and sodium metabisulfite.

Humectants and Moisturizers

The compositions of the present invention can also contain one or more humectants or moisturizers. A variety of these materials can be employed and each can be present at a level of from about 0.1% to about 20%, more preferably from about 0.5% to about 10%, and most preferably from about 1% to about 5%. These materials include guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. An especially preferred humectant or moisturizer material for use herein is glycerol.

Emulsifiers

The compositions herein can contain various emulsifiers. These emulsifiers are useful for emulsifying the various topical carrier components of the compositions herein. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerol, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, Steareth-21, Steareth-2, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof.

The emulsifiers can be used individually or as a mixture of two or more and can comprise from about 0.1% to about 10%, more preferably from about 1% to about 7%, and most preferably from about 1% to about 5% of the compositions of the present invention.

Crosslinked Polyacrylate and Polyacrylamide Polymers

Crosslinked polyacrylate and polyacrylamide polymers are useful as thickeners herein and include both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon- carbon double bond or other such polymerizable functional group, l is an integer of 0 or greater, m is an integer of 0 or greater, n is an integer of 0 or greater, but where either l or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, and most preferably $C_1$–$C_2$. When quaternized, the polymers are preferably quaternized with short chain alkyls, i.e., $C_1$–$C_8$, preferably $C_1$–$C_5$, more preferably $C_1$–$C_3$, and most preferably $C_1$–$C_2$. The acid addition salts refer to polymers having protonated amino groups. Acid addition salts can be performed through the use of halogen (e.g., chloride), acetic, phosphoric, nitric, citric, or other acids.

These $(A)_l(B)_m(C)_n$ polymers also comprise a crosslinking agent, which is most typically a material containing two or more unsaturated is functional groups. The crosslinking agent is reacted with the monomer units of the polymer and is incorporated into the polymer, thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g., viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects in water or other aqueous carriers of the compositions hereof. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc., Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l(B)_m(C)_n$ wherein l is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare® SC92 from Allied Colloids Ltd. (Norfolk, Va.). This polymer has the proposed CTFA designation, "Polyquaternium 32 (and) Mineral Oil".

Other cationic polymers, useful herein, are those not containing acrylamide or other (C) monomers, that is, n is zero. In these polymers the (A) and (B) monomer components are as described above. An especially preferred group of these non-acrylamide containing polymers is one in which l is also zero. In this instance the polymer is essentially a homopolymer of a dialkylaminoalkyl methacrylate monomer or its quaternary ammonium or acid addition salt. These diaklylaminoalkyl methacrylate polymers preferably contain a crosslinking agent as described above.

A cationic polymer, which is essentially a homopolymer, useful herein, is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd, (Norfolk, Va.) under the trademark Salcare® SC95. This polymer has recently been given the CTFA designation "Polyquaternium 37 (and) Mineral Oil (and) PPG-1 Trideceth-6."

Also useful herein are polyacrylamide polymers, especially non-ionic polyacrylamide polymers including substituted branched or unbranched polymers. These polymers can be formed from a variety of monomers including acrylamide and methacrylamide which are unsubstituted or substituted with one or two alkyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Polysaccharides

A wide variety of polysaccharides are useful herein. The term "polysaccharides" means polymeric materials containing a backbone of repeating sugar (i.e., carbohydrate) units. Nonlimiting examples of polysaccharide include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroyxalkylated (preferably hydroxyethylated or hydroxypropylated) to form a hydroxyalkylated cellulose which is then further modified with a C10–C30 straight chain or branched chain alkyl group through an ether linkage. Typically these polymers are ethers of C10–C30 straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e., alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1→3) linked glucose units with a (1→6) linked glucose every three units, a commercially available example of which is Clearogel™ CS11 from Michel Mercier Products Inc. (Mountainside, N.J.).

Gums

A wide variety of gums are also useful in the compositions of the present invention. These gums are primarily derived from natural sources. Nonlimiting examples of gums include materials selected from the group consisting of acacia, agar, algin, alginic acid, ammonium alginate, amylopectin, bentonite, calcium alginate, calcium carrageenan, carnitine, carrageenan, corn starch, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, magnesium aluminum silicate, manesium silicate, magnesium trisilicate, montmorillonite, natto gum, potassium alginate, potassium carrageenan, propylene glycol alginate, sclerotium gum, sodium carboxymethyl dextran, sodium carrageenan, sodium polyacrylate starch, sodium silicoaluminate, starch/acrylates/acrylamide copolymer, tragacanth gum, xanthan gum, and mixtures thereof.

Silica

The compositions of the present invention can also contain silica as a thickening agent for the topical carrier. The silica can be either untreated or surface treated with a hydrophobic material such as a polyalkylsiloxane.

A preferred silica is a fumed silica that has been surface treated with a polydimethylsiloxane. A commercially available example of this material is sold under the trade name CAB-O-Sil® TS-720 Treated Fumed Silica by Cabot Corporation, Tuscola, Ill. This material has a surface area of 100±20 $m^2/g$ and a bulk density of 50 g/liter. See Cabot Corporation Technical Data Sheet Pamphlets Entitled "CAB-O-Sil® TS-720 Treated Fumed Silica," 1991, and "CAB-O-Sil® Fumed Silica In Cosmetic and Personal Care Products", TD-104, March 1992, which are both incorporated by reference herein in their entirety.

Oils

The compositions of the present invention can also optionally comprise various oil materials, that is, a material generally having low solubility in water, generally less than about 1% by weight at 25° C. Examples of suitable oil components include, but are not limited to, volatile and non-volatile silicone oils, highly branched hydrocarbons, and non-polar carboxylic acid and alcohol esters, and mixtures thereof. Oils useful in the instant invention are further described in U.S. Pat. No. 4,919,934, to Deckner et al., issued Apr. 24 1990, which is incorporated herein by reference in its entirety.

Volatile silicone components such as cyclic polydimethylsiloxanes containing from about 3 to about 9 silicon atoms, and dimethicone are useful herein. Nonvolatile silicones include polyalkylsiloxanes and polyalkylaryl siloxanes. Useful volatile and nonvolatile silicones are disclosed in U.S. Pat. No. 5,069,897, to Orr, issued Dec. 3, 1991, which is incorporated by reference herein in its entirety.

Other Additional Components

The compositions of the present invention can comprise a wide range of other additional components. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin protectants, solvents, suspending agents (nonsurfactant), ultraviolet light absorbers, and viscosity increasing agents (aqueous and nonaqueous). Examples of other functional classes of materials useful herein that are well known to one of ordinary skill in the art include emulsifiers, solubilizing agents, and sequestrants, and the like.

Nonlimiting examples of these additional components cited in the *CTFA Cosmetic Ingredient Handbook*, as well as other materials useful herein, include the following: vitamins and derivatives thereof [e.g., vitamin C, Vitamin A (i.e., retinoic acid), retinol, retinoids, and the like]; antioxidants; polyethyleneglycols and polypropyleneglyocis; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; antioxidants; chelators and sequestrants; and aesthetic components such as fragrances, pigments, colorings, essential oils, skin senates, astringents, skin soothing agents, skin healing agents and the like, nonlimiting examples of these aesthetic components include clove oil, menthol, camphor, eucalyptus oil, eugenol, menthyl lactate, witch hazel distillate, bisabolol, dipotassium glycyrrhizinate, and the like.

METHODS OF PROTECTING THE SKIN

The topical sunscreening compositions of the present invention are used in conventional ways to provide protection to the skin from the harmful effects of ultraviolet radiation, and to provide any additional cosmetic or pharmaceutical benefits appropriate to the product such as anti-acne benefits, anti-wrinkle and anti-skin aging benefits, artificial tanning, analgesic benefits, and the like. Such methods of use depend upon the type of composition employed, but generally involve application of an effective amount of the product to the skin. The term "effective amount" means an amount sufficient to provide the benefit desired. Typical amounts of the compositions of the present invention which are applied to the skin will vary depending upon the type of composition and the benefit desired, however, typical ranges are generally from about 0.1 $mg/cm^2$ to about 25 $mg/cm^2$, with about 2 $mg/cm^2$ being typical.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example 1

Low pH Sunscreen Lotion

A sunscreen lotion is prepared by combining the following ingredients using conventional mixing techniques.

| Ingredients | Weight Percent |
| --- | --- |
| Phase A | |
| PPG-14 Butyl Ether | 8.00 |
| Benzoic Acid | 2.00 |
| Phase B | |
| Water | QS100 |
| 2-Phenylbenzimidazole-5-Sulfonic Acid | 2.00 |
| Distearyl Dimethyl Ammonium Chloride | 0.150 |
| Tetrasodium EDTA | 0.020 |

-continued

| Ingredients | Weight Percent |
| --- | --- |
| Phase C | |
| Polyacrylamide (and) Isoparaffin (and) Laureth-7[1] | 3.00 |

[1]Available as Sepigel 305 from Seppic Corporation, Fairfield, NJ.

In a suitable vessel, the phase A ingredients are combined and heated with mixing to 75° C. until a liquid oil phase is formed. In a separate vessel, the phase B ingredients are heated with mixing to 75° C. to form a water phase. Next, the oil phase is added to the water phase with mixing to form an emulsion. Next, the phase C ingredient is added to the emulsion with mixing and then cooled to room temperature.

This composition has a pH of about 2.6 to about 3.0 and is useful for topical application to the skin to provide protection from the harmful effects of ultraviolet radiation.

In an alternate procedure, the 2-phenylbenzimidazole-5-sulfonic acid is incorporated in with phase A.

Example 2
Low pH Sunscreen Lotion

A sunscreen lotion is prepared by combining the following ingredients using conventional mixing techniques.

| Ingredients | Weight Percent |
| --- | --- |
| Phase A | |
| C12–15 Alkyl Benzoate | 8.50 |
| PPG-14 Butyl Ether | 3.00 |
| Salicylic Acid | 2.00 |
| Polydimethylsiloxane Treated Fumed Silica[1] | 0.90 |
| Steareth-2 | 0.65 |
| Polypropylene[2] | 0.50 |
| Phase B | |
| Water | QS100 |
| 2-Phenylbenzimidazole-5-Sulfonic Acid | 1.00 |
| Hydroxyethylcellulose | 0.20 |
| Triethanolamine | 0.10 |
| Tetrasodium EDTA | 0.02 |
| Phase C | |
| Polyquaternium 37 (and) Mineral Oil (and) PPG-1 trideceth-6[3] | 2.00 |
| Phase D | |
| Dimethicone (and) dimethiconol[4] | |
| Phase E | |
| Fragrance | 0.20 |

[1]Available as CAB-O-Sil ® TS-720 from Cabot Corporation, Tuscola, IL.
[2]Available as Propylmatte from Micro Powders, Tarrytown, NY.
[3]Available as Salcare SC95 from Allied Colloids, Norfolk, VA.
[4]Available as Q21403 from Dow Corning which is a mixture of 85% dimethicone and 15% dimethiconol.

In a suitable vessel, the phase A ingredients are combined and heated with mixing to 75° C. until a liquid oil phase is formed. In a separate vessel, the phase B ingredients are heated with mixing to 75° C. to form a water phase. Next, the oil phase is added to the water phase with mixing to form an emulsion. Next, the phase C ingredient is added to the emulsion with mixing and then cooled to room temperature. Next, the phase D and E ingredients are added with mixing.

This composition has a pH of about 2.6 to about 3.0 and is useful for topical application to the skin to provide protection from the harmful effects of ultraviolet radiation.

In an alternate procedure, the 2-phenylbenzimidazole-5-sulfonic acid is incorporated in with phase A.

Example 3
Low pH Sunscreen Lotion

A sunscreen lotion is prepared by combining the following ingredients using conventional mixing techniques.

| Ingredients | Weight Percent |
| --- | --- |
| Phase A | |
| Octyl Methoxycinnamate | 7.50 |
| PPG-14 Butyl Ether | 3.00 |
| Salicylic Acid | 2.00 |
| Tocopherol Acetate | 1.00 |
| Polydimethylsiloxane Treated Fumed Silica[1] | 0.90 |
| Polypropylene[2] | 0.50 |
| Steareth-21 | 0.45 |
| Steareth-2 | 0.45 |
| Phase B | |
| Water | QS100 |
| 2-Phenylbenzimidazole-5-Sulfonic Acid | 1.00 |
| Glycerol | 1.50 |
| Hydroxyethylcellulose | 0.20 |
| Triethanolamine | 0.10 |
| Tetrasodium EDTA | 0.02 |
| Phase C | |
| Polyquaternium 37 (and) Mineral Oil (and) PPG-1 trideceth-6[3] | 2.00 |
| Phase D | |
| Dimethicone (and) Dimethiconol[4] | 1.50 |
| Phase E | |
| Fragrance | 0.20 |

[1]Available as CAB-O-Sil ® TS-720 from Cabot Corporation, Tuscola, IL.
[2]Available as Propylmatte from Micro Powders, Tarrytown, NY.
[3]Available as Salcare SC95 from Allied Colloids, Norfolk, VA.
[4]Available as Q21403 from Dow Corning which is a mixture of 85% dimethicone and 15% dimehticonol.

In a suitable vessel, the phase A ingredients are combined and heated with mixing to 75° C. until a liquid oil phase is formed. In a separate vessel, the phase B ingredients are heated with mixing to 75° C. to form a water phase. Next, the oil phase is added to the water phase with mixing to form an emulsion. Next, the phase C ingredient is added to the emulsion with mixing and then cooled to room temperature. Next, the phase D and E ingredients are added with mixing.

This composition has a pH of about 2.6 to about 3.0 and is useful for topical application to the skin to provide protection from the harmful effects of ultraviolet radiation.

In an alternate procedure, the 2-phenylbenzimidazole-5-sulfonic acid is incorporated in with phase A.

Example 4
Low pH Sunscreen Composition Containing Dihydroxyacetone

A sunscreen composition containing the artificial tanning active dihydroxyacetone is prepared using conventional mixing techniques.

| Ingredients | Weight Percent |
| --- | --- |
| Phase A | |
| Octyl Methoxycinnamate | 3.50 |
| Polyquaternium 37 (and) Mineral Oil (and) PPG-1 Trideceth 6 | 1.75 |
| 2-Phenylbenzimidazole-5-Sulfonic Acid | 1.50 |
| Octocrylene | 1.00 |
| PVP Eicosene Copolymer | 1.00 |

-continued

| Ingredients | Weight Percent |
|---|---|
| Isohexadecane | 1.00 |
| Glyceryl Tribehenate | 0.75 |
| Cetyl Palmitate | 0.75 |
| Cetyl Alcohol | 0.50 |
| Phase B | |
| Water | QS100 |
| Distearyl Dimethyl Ammonium Chloride | 0.20 |
| Hydroxyethylcellulose | 0.20 |
| Disodium EDTA | 0.05 |
| Phase C | |
| Water | 2.00 |
| Butylene Glycol | 2.00 |
| DMDM Hydantoin (and) | 0.20 |
| Iodopropynyl Carbamate | |
| Phase D | |
| Water | 6.00 |
| Dihydroxyacetone | 3.00 |
| Phase E | |
| Cyclomethicone | 2.00 |
| Phase F | |
| Fragrance | 1.00 |

[1]Available as Salcare® SC95 from Allied Colloids Ltd. (Norfolk, VA).

In a suitable vessel, the phase A ingredients are combined and heated with mixing to 80–85° C. to form an oil phase. In a separate vessel, the phase B, ingredients are heated with mixing to 70–75° C. to form an oil phase. Next, the oil phase is added to the water phase with mixing to form the emulsion. The mixture is then mixed while cooling to 40° C. In a separate vessel the phase C ingredients are combined and added to the emulsion with mixing. In another vessel, the phase D ingredients are combined and added to the emulsion with mixing and then cooled to room temperature. Next the Phase E ingredient and the Phase F ingredient are added with mixing.

This composition has a pH of about 3.5 to about 4.5 and is useful for topical application to the skin to provide protection from the harmful effects of ultraviolet radiation and also to provide an artificial tan.

What is claimed is:

1. A topical sunscreen composition having a pH of from about 1 to 4 comprising:
   (a) from about 0.05% to about 10% of 2-phenylbenzimidazole-5-sulfonic acid, and
   (b) from about 20% to about 99.95% of a topical carrier, wherein the 2-phenylbenzimidazole-5-sulfonic acid is substantially present in free acid form in the composition.

2. A composition according to claim 1 wherein said emulsion is a water-in-oil-in-water emulsion.

3. A composition according to claim 1 wherein said emulsion is an oil-in-water-in-silicone emulsion.

4. A composition according to claim 1 which comprises from about 0.5% to about 10% of 2-phenylbenzimidazole-5-sulfonic acid.

5. A composition according to claim 1 which comprises from about 1% to about 4% of 2-phenylbenzimidazole-5-sulfonic acid.

6. A composition according to claim 1 wherein said topical carrier is an emulsion.

7. A composition according to claim 6 wherein said emulsion is an oil-in-water emulsion.

8. A composition according to claim 1 wherein said emulsion is a water-in-oil emulsion.

9. A composition according to claim 7 which further comprises a pharmaceutical active selected from the group consisting of anti-acne actives, anti-skin wrinkling actives, non-steroidal anti-inflammatory drugs, antipruritic drugs, anesthetic drugs, antimicrobial drugs, additional sunscreening agents, sunless tanning agents, skin bleaching agents, and mixtures thereof.

10. A composition according to claim 9 wherein said pharmaceutical active is an anti-skin wrinkling active selected from the group consisting of salicylic acid, glycolic acid, lactic acid, retinoic acid, and mixtures thereof.

11. A composition according to claim 10 wherein said anti-skin wrinkling active is salicylic acid.

12. A composition according to claim 7 which further comprises from about 0.1% to about 20% of a humectant.

13. A composition according to claim 12 wherein said humectant is glycerol.

14. A composition according to claim 9 wherein said pharmaceutical active is an additional sunscreen agent selected from the group consisting of 2-ethylhexyl p-methoxycinnamate, 2-ethylhexyl N,N-dimethyl-p-aminobenzoate, p-aminobenzoic acid, octocrylene, oxybenzone, homomenthyl salicylate, octyl salicylate, 4,4'-methoxy-butyldibenzoylmethane, 4-isopropyl dibenzoylmethane, 3-benzylidene camphor, 3-(4-methylbenzylidene) camphor, triethanolamine salicylate, titanium dioxide, zinc oxide, silica, iron oxide, 4-N,N-(2-ethylhexyl)methyl-aminobenzoic acid ester of 2,4-dihydroxybenzophenone, 4-N,N-(2-ethylhexyl) methylaminobenzoic acid ester with 4-hydroxydibenzoylmethane, 4-N, N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

15. A method for providing protection to the skin of a human from the effects of ultraviolet radiation, said method comprising topically applying to the skin a composition according to claim 1 in an amount effective to provide ultraviolet protection.

16. A method for providing protection to the skin of a human from the effects of ultraviolet radiation, said method comprising topically applying to the skin a composition according to claim 7 in an amount effective to provide ultraviolet protection.

17. A method for providing protection to the skin of a human from the effects of ultraviolet radiation, said method comprising topically applying to the skin a composition according to claim 11 in an amount effective to provide ultraviolet protection.

18. A method for providing protection to the skin of a human from the effects of ultraviolet radiation, said method comprising topically applying to the skin a composition according to claim 14 in an amount effective to provide ultraviolet protection.

* * * * *

UNITED STATES PATENT AND TRADEMARK OFFICE
CERTIFICATE OF CORRECTION

PATENT NO. : 6,153,176
DATED : November 28, 2000
INVENTOR(S) : J.E. Kaleta et al.

It is certified that error appears in the above-identified patent and that said Letters Patent is hereby corrected as shown below:

<u>Column 18,</u>
Line 29, "4,4'-methoxy-butyldibenzoylmethane" should read -- 4,4'-methoxy-t-butyldibenzoylmethane --.
Line 33, "4-N,N-(2-ethylhexyl)methyl-aminobenzoic" should read -- 4-N,N-(2-ethylhexyl)methylaminobenzoic --.
Line 37, "4-N,N-(2-ethylhexyl)methylaminobenzoic" should read -- 4-N,N-(2-ethylhexy)methylaminobenzoic --.

Signed and Sealed this

Twenty-second Day of March, 2005

JON W. DUDAS
*Director of the United States Patent and Trademark Office*